(12) United States Patent
Tornier et al.

(10) Patent No.: US 8,187,282 B2
(45) Date of Patent: May 29, 2012

(54) ANCILLARY TOOL FOR POSITIONING A GLENOID IMPLANT

(75) Inventors: Alain Tornier, Saint Ismier (FR); Anders Ekelund, Bromma (SE); Laurent Comtat, Fontaine (FR)

(73) Assignee: Tornier SAS, Saint Ismier (FR)

(*) Notice: Subject to any disclaimer, the term of this patent is extended or adjusted under 35 U.S.C. 154(b) by 1343 days.

(21) Appl. No.: 11/770,285

(22) Filed: Jun. 28, 2007

(65) Prior Publication Data

US 2007/0250174 A1 Oct. 25, 2007

Related U.S. Application Data

(62) Division of application No. 10/793,947, filed on Mar. 8, 2004, now Pat. No. 7,887,544.

(60) Provisional application No. 60/453,972, filed on Mar. 13, 2003.

(30) Foreign Application Priority Data

Mar. 10, 2003  (FR) ...................................... 03 02936

(51) Int. Cl.
 *A61B 17/56* (2006.01)
(52) U.S. Cl. ....................................................... 606/99
(58) Field of Classification Search ................... 606/53, 606/96–99, 102, 104, 86 A, 86 B; 623/19.11–19.13, 623/22.11, 22.12, 22.21, 22.36, 22.38
 See application file for complete search history.

(56) References Cited

U.S. PATENT DOCUMENTS

| | | | |
|---|---|---|---|
| 2,666,430 A | 1/1954 | Gispert | |
| 3,694,820 A | 10/1972 | Scales et al. | |
| 3,815,157 A | 6/1974 | Skorecki et al. | |
| 3,842,442 A | 10/1974 | Kolbel | |
| 3,864,758 A | 2/1975 | Skobel | |
| 3,869,730 A | 3/1975 | Skobel | |
| 3,916,451 A | 11/1975 | Buechel et al. | |
| 3,978,528 A | 9/1976 | Crep | |
| 3,979,778 A | 9/1976 | Stroot | |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A | 12/1979 | Gristina | |

(Continued)

FOREIGN PATENT DOCUMENTS

CH 426096 12/1966

(Continued)

OTHER PUBLICATIONS

Christian Gerber, et al.; Brochure; "Anatomical Shoulder System Surgical Technique, Removable head option for improved surgical results", Zimmer, Inc.; 2004; 33 pages.

(Continued)

*Primary Examiner* — Eduardo C Robert
*Assistant Examiner* — David Comstock
(74) *Attorney, Agent, or Firm* — Faegre Baker Daniels LLP (57) ABSTRACT

The ancillary tool according to the invention comprises a plate which defines a convex surface intended to bear against the glenoid cavity of a patient's scapula and which forms a directional guide for a drilling, fashioning or like member. To allow the surgeon to apply this member in a chosen direction, the tool comprises means for adjusting the position of the guide with respect to the plate.

20 Claims, 5 Drawing Sheets

U.S. PATENT DOCUMENTS

| | | |
|---|---|---|
| 4,206,517 A | 6/1980 | Pappas et al. |
| 4,261,062 A | 4/1981 | Amstutz et al. |
| 4,325,373 A | 4/1982 | Slivenko et al. |
| 4,550,450 A | 11/1985 | Kinnett |
| 4,693,723 A | 9/1987 | Gabard |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazzeri et al. |
| 5,030,219 A | 7/1991 | Matsen, III et al. |
| 5,032,132 A | 7/1991 | Matsen, III et al. |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,171,289 A | 12/1992 | Tornier |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,261,914 A | 11/1993 | Warren |
| 5,314,479 A | 5/1994 | Rockwood, Jr. et al. |
| 5,314,485 A | 5/1994 | Judet |
| 5,314,487 A | 5/1994 | Schryver et al. |
| 5,326,359 A | 7/1994 | Oudard |
| 5,330,531 A | 7/1994 | Capanna |
| 5,358,526 A | 10/1994 | Tornier |
| 5,383,936 A | 1/1995 | Kubein-Meesenburg et al. |
| 5,405,399 A | 4/1995 | Tornier |
| 5,425,779 A | 6/1995 | Schlosser |
| 5,429,639 A | 7/1995 | Judet |
| 5,443,519 A | 8/1995 | Averill et al. |
| 5,458,650 A | 10/1995 | Carret et al. |
| 5,462,563 A | 10/1995 | Shearer et al. |
| 5,505,731 A | 4/1996 | Tornier |
| 5,507,817 A | 4/1996 | Craig et al. |
| 5,507,818 A | 4/1996 | McLaughlin |
| 5,507,824 A | 4/1996 | Lennox |
| 5,549,682 A | 8/1996 | Roy |
| 5,580,352 A | 12/1996 | Sekel |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,702,486 A | 12/1997 | Craig et al. |
| 5,723,018 A | 3/1998 | Cyprien et al. |
| 5,728,161 A | 3/1998 | Camino et al. |
| 5,741,335 A | 4/1998 | Gerber et al. |
| 5,755,807 A | 5/1998 | Anstaett et al. |
| 5,766,256 A | 6/1998 | Oudard et al. |
| 5,769,856 A | 6/1998 | Dong et al. |
| 5,800,551 A | 9/1998 | Williamson et al. |
| 5,824,106 A | 10/1998 | Fournol |
| 5,879,395 A | 3/1999 | Tornier et al. |
| 5,879,405 A | 3/1999 | Ries et al. |
| 5,902,340 A | 5/1999 | White et al. |
| 5,910,171 A | 6/1999 | Kummer et al. |
| 5,928,285 A | 7/1999 | Bigliani et al. |
| 5,944,758 A | 8/1999 | Mansat et al. |
| 5,961,555 A | 10/1999 | Huebner |
| 5,984,927 A | 11/1999 | Wenstrom, Jr. et al. |
| 6,007,535 A | 12/1999 | Rayhack et al. |
| 6,015,437 A | 1/2000 | Stossel |
| 6,033,439 A | 3/2000 | Camino et al. |
| 6,045,582 A | 4/2000 | Prybyla |
| 6,045,583 A | 4/2000 | Gross et al. |
| 6,102,953 A | 8/2000 | Huebner |
| 6,129,764 A | 10/2000 | Servidio |
| 6,162,254 A | 12/2000 | Timoteo |
| 6,165,224 A | 12/2000 | Tornier |
| 6,168,629 B1 | 1/2001 | Timoteo |
| 6,171,341 B1 | 1/2001 | Boileau et al. |
| 6,183,519 B1 | 2/2001 | Bonnin et al. |
| 6,197,062 B1 | 3/2001 | Fenlin |
| 6,197,063 B1 | 3/2001 | Dews |
| 6,203,575 B1 | 3/2001 | Farey |
| 6,206,925 B1 | 3/2001 | Tornier |
| 6,228,120 B1 | 5/2001 | Leonard et al. |
| 6,267,767 B1 | 7/2001 | Strobel et al. |
| 6,283,999 B1 | 9/2001 | Rockwood, Jr. |
| 6,299,646 B1 | 10/2001 | Chambat et al. |
| 6,312,467 B1 | 11/2001 | McGee |
| 6,328,758 B1 | 12/2001 | Tornier et al. |
| 6,334,874 B1 | 1/2002 | Tornier et al. |
| 6,364,910 B1 | 4/2002 | Schultz et al. |
| 6,368,352 B1 | 4/2002 | Camino et al. |
| 6,368,353 B1 | 4/2002 | Arcand |
| 6,379,386 B1 | 4/2002 | Resch et al. |
| 6,379,387 B1 | 4/2002 | Tornier |
| 6,398,812 B1 | 6/2002 | Masini |
| 6,406,495 B1 | 6/2002 | Schoch |
| 6,406,496 B1 | 6/2002 | Rüter |
| 6,436,144 B1 | 8/2002 | Ahrens |
| 6,436,147 B1 | 8/2002 | Zweymuller |
| 6,454,809 B1 | 9/2002 | Tornier |
| 6,458,136 B1 | 10/2002 | Allard et al. |
| 6,475,243 B1 | 11/2002 | Sheldon et al. |
| 6,488,712 B1 | 12/2002 | Tornier et al. |
| 6,494,913 B1 | 12/2002 | Huebner |
| 6,506,214 B1 | 1/2003 | Gross |
| 6,508,840 B1 | 1/2003 | Rockwood, Jr. et al. |
| 6,514,287 B2 | 2/2003 | Ondrla et al. |
| 6,520,994 B2 | 2/2003 | Nogarin |
| 6,530,957 B1 | 3/2003 | Jack |
| 6,540,770 B1 | 4/2003 | Tornier et al. |
| 6,558,425 B2 | 5/2003 | Rockwood |
| 6,569,202 B2 | 5/2003 | Whiteside |
| 6,582,469 B1 | 6/2003 | Tornier |
| 6,589,281 B2 | 7/2003 | Hyde, Jr. |
| 6,599,295 B1 | 7/2003 | Tornier et al. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,673,115 B2 | 1/2004 | Resch et al. |
| 6,679,916 B1 | 1/2004 | Frankle et al. |
| 6,736,851 B2 | 5/2004 | Maroney et al. |
| 6,746,487 B2 | 6/2004 | Scifert et al. |
| 6,749,637 B1 | 6/2004 | Bahler |
| 6,755,866 B2 | 6/2004 | Southworth |
| 6,761,740 B2 | 7/2004 | Tornier |
| 6,767,368 B2 | 7/2004 | Tornier |
| 6,780,190 B2 | 8/2004 | Maroney |
| 6,783,549 B1 | 8/2004 | Stone et al. |
| 6,790,234 B1 | 9/2004 | Frankle |
| 6,802,864 B2 | 10/2004 | Tornier |
| 6,824,567 B2 | 11/2004 | Tornier et al. |
| 6,863,690 B2 | 3/2005 | Ball et al. |
| 6,875,234 B2 | 4/2005 | Lipman et al. |
| 6,887,277 B2 | 5/2005 | Rauscher et al. |
| 6,890,357 B2 | 5/2005 | Tornier |
| 6,890,358 B2 | 5/2005 | Ball et al. |
| 6,942,699 B2 | 9/2005 | Stone et al. |
| 6,953,478 B2 | 10/2005 | Bouttens et al. |
| 6,969,406 B2 | 11/2005 | Tornier |
| 7,011,686 B2 | 3/2006 | Ball et al. |
| 7,033,396 B2 | 4/2006 | Tornier |
| 7,066,959 B2 | 6/2006 | Errico et al. |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |

| | | |
|---|---|---|
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2004/0006392 A1 | 1/2004 | Grusin et al. |
| 2004/0034431 A1 | 2/2004 | Maroney et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210220 A1 | 10/2004 | Tornier |
| 2004/0210317 A1 | 10/2004 | Maroney et al. |
| 2004/0215200 A1 | 10/2004 | Tornier |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256584 A1 | 11/2005 | Farrar |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat et al. |
| 2006/0020344 A1 | 1/2006 | Shultz et al. |
| 2006/0030946 A1 | 2/2006 | Ball et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0043265 A1 | 2/2007 | Rochetin |
| 2007/0173947 A1 | 7/2007 | Ratron et al. |
| 2007/0179628 A1 | 8/2007 | Rochetin |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |

FOREIGN PATENT DOCUMENTS

| | | |
|---|---|---|
| CH | 507704 | 5/1971 |
| DE | 19509037 | 9/1996 |
| DE | 19630298 | 1/1998 |
| EP | 0257359 | 3/1988 |
| EP | 0299889 | 1/1989 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797694 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 | 1/2001 |
| EP | 1195149 | 4/2002 |
| EP | 1380274 | 1/2004 |
| EP | 1402854 | 3/2004 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 01/47442 | 7/2001 |
| WO | WO 02/39931 | 5/2002 |
| WO | WO 02/39933 | 5/2002 |
| WO | WO 02/067821 | 9/2002 |
| WO | WO 03/005933 | 1/2003 |
| WO | WO03/094806 | 11/2003 |
| WO | WO 2007/109319 | 9/2007 |
| WO | WO 2007/109340 | 9/2007 |
| WO | WO 200707/109291 | 9/2007 |

OTHER PUBLICATIONS

Non-final Rejection dated Feb. 22, 2006 from U.S. Appl. No. 10/793,947; 12 pages.
Ferrand et al., U.S. Appl. No. 11/735,027, entitled "Glenoid Component with an Anatomically Optimized Keel," filed Apr. 13, 2007.
Rochetin et al., U.S. Appl. No. 11/401,415, entitled "Surgical Apparatus for Implantation of a Partial or Total Knee Prosthesis," filed Apr. 11, 2006.
Boileau et al., U.S. Appl. No. 12/020,913, entitled "Method and Apparatus for Fitting a Shoulder Prosthesis" filed Jan. 28, 2008.
John M. Fenlin Jr., M.D., Symposium on Surgery of the Shoulder, "Total Glenohumeral Joint Replacement," *Orthopedic Clinics of North America*, vol. 6, No. 2, Apr. 1975, pp. 565-583.
"Aequalis-Fracture Suture Technique in 5 Steps," Tornier, Inc., 2 pp.
"Aequalis-Fracture Shoulder Prosthesis—Surgical Technique," Tornier, Inc., 32 pp.
"Aequalis® Press-Fit Shoulder Prosthesis—Surgical Technique," Tornier, Inc., 27 pp.
"Anatomical Shoulder™—Cemented Shoulder Prosthesis Product Information and Surgical Technique," Sulzer Medica, 2000, 30 pp.
"Anatomical Shoulder™ System Surgical Technique—Removable head option for improved surgical results," Zimmer, Inc., 2004, 33 pp.
Bigliani/Flatow®—The Complete Shoulder Solution, 4-Part Fracture of the Humerus Surgical Technique, Zimmer, Inc., 2000, 18 pp.
"Bio-Modular® / Bi-Polar Shoulder Arthroplasty," Biomet, Inc., 1997, 2 pp.

"Bio-Modular® Choice, Shoulder System," Biomet Orthopedics, Inc., 2004, 16 pp.

"Bio-Modular Total Shoulder Surgical Technique," Biomet Orthopedics, Inc., 2001, 12 pp.

"Copeland™ Humeral Resurfacing Head," Biomet Orthopedics, Inc., 2001, 12 pp.

"Global C.A.P.™ Surgical technique, resurfacing humeral head implant," DePuy International, Ltd., 2004, 23 pp.

Boileau, et al. "Adaptability and modularity of shoulder prosthesis," *Maitrise Orthopédique*, https://www.maitriseorthop.com/corpusmaitri/orthopaedic/prothese_epaule_orthop/boileau_us.shtml, Jan. 3, 2006, 14 pp.

Boileau, et al. "Arthroscopic Repair of Full-Thickness Tears of the Supraspinatus: Does the tendon really heal?," *The Journal of Bone and Joint Surgery, Inc.*, pp. 1229-1240, 2005, 12 pp.

"Design Rationale," Latitude®, 36 pp.

Klein, Travis J., et al. "Mechanically favorable bone remodeling in rotator cuff arthropathy patients with good function," *Minneapolis Sports Medicine Center and University of Minnesota*, 2 pp.

Mansat, Michel, "Neer 3™, Surgical Technique for Fractrures," Smith & Nephew, 2000, 19 pp.

Molé, M.D., et al., "Aequalis-Reversed™ Shoulder Prosthesis, Surgical Technique," Tornier, Inc., 24 pp.

Nicholson, Gregory P., "Arthroplasty and Rotator Cuff Deficiency," Chapter 7, pp. 149-166.

"Offset Head, Bio-Modular® Total Shoulder," Biomet, Inc. 2000, 2 pp.

"The Foundation® Total Shoulder System," Encore Surgical, 2 pp.

"The Townley Modular Shoulder, Design by Reason," Biopro, Inc., 2 pp.

Zimmer® Bigliani/Flatow®—The Complete Shoulder Solution, Total Shoulder Arthroplasty Surgical Technique, Zimmer, Inc., 2003, pp. 1-30.

"Zimmer® Shoulder Retractors," Zimmer, Inc., 2000, 2 pp.

"Anatomic Glenoid, Surgical Technique," Smith & Nephew, 2000, 6 pp.

"Anatomical Shoulder™ System—The new removable head option," Zimmer Inc., 2004, 6 pp.

"Delta CTA™ Reverse Shoulder Prosthesis," DePuy International, Ltd., 2004, 28 pp.

Cofield, M.D., Robert H. "Cofield[2] Total Shoulder System, Surgical Technique," Smith & Nephew, 1997, 32 pp.

"Aequalis®-Glenoid Keeled and Pegged—Surgical Technique," Tornier, Inc., 12 pp.

"Bigliani/Flatow®—The Complete Shoulder Solution, Designed by Shoulder Surgeons for Shoulder Surgery," Zimmer, Inc., 2001, 6 pp.

"Tornier Aequalis® Reversed 2 Prong Capsular Retractor," Tornier, Inc., Oct. 8, 2005.

"Tornier Aequalis® Reversed Shoulder G2 Baseplate," Tornier, Inc., Oct. 8, 2005.

"Tornier Surgical Technique Addendum, Tornier Aequalis® Reversed Hemi-Adaptor Technique," Tornier, Inc., Aug. 8, 2005, 1 pg.

"Tornier Surgical Technique Addendum, Aequalis® Reversed Shoulder Polyethylene Insert," Tornier, Inc., Aug. 8, 2005, 1 pg.

Beuchel M.D., Frederick F. "Beuchel-Pappas™ Modular Salvage Shoulder System," Endotec, Inc., 2000, 8 pp.

Beuchel M.D., Frederick F. "Beuchel-Pappas™ Resurfacing Shoulder System," Endotec, Inc., 2000, 9 pp.

Beuchel M.D., Frederick F. "Beuchel-Pappas™ Total Shoulder System," Endotec, Inc., 2000, 16 pp.

Hertel M.D., PD, Ralph. "Technical considerations for implantation of EPOCA glenoid components (Leseprobe)," *Epoca Newsletter*, May 14, 2001, 1 pg.

Apoil, André "A Condyle for the Rotator Cuff Muscles, the total shoulder prosthesis," Aesculap®, 1994, 4 pp.

ANCILLARY TOOL FOR POSITIONING A GLENOID IMPLANT

REFERENCE TO RELATED APPLICATION

The present application is a divisional of U.S. patent application Ser. No. 10/793,947, filed Mar. 8, 2004, now issued U.S. Pat. No. 7,887,544, entitled "Ancillary Tool For Positioning a Glenoid Implant", which claims the benefit of U.S. Provisional application Ser. No. 60/453,972, filed Mar. 13, 2003, and claims priority to French application no. 0302936, filed Mar. 10, 2003, the entire disclosures of which are hereby incorporated by reference for all purposes.

FIELD OF THE INVENTION

The present invention relates to an ancillary tool for positioning a glenoid implant.

BACKGROUND OF THE INVENTION

When implanting a shoulder prosthesis, it is sometimes necessary to position at the articular end of a patient's scapula a glenoid implant which, on one side, is rigidly anchored in the scapula and which, on the other side, defines an articular surface for cooperation with the head of a humeral implant fixed to the corresponding end of the patient's humerus. In order to anchor the glenoid implant firmly in the scapula, this implant generally comprises a keel projecting from the rest of the implant and intended to be received and immobilized in a canal hollowed out inside the scapula with the aid of an appropriate member, particularly the bit of a surgical drill. When this member is applied on the scapula, an ancillary guiding tool is currently used, which limits the risks of slipping of the stem or tip of this member.

Document U.S. Pat. No. B1-6,379,386 describes such guiding tools. In particular, referring to FIGS. 5 to 9 thereof, this document describes a tool for guiding the bit of a drill, comprising a plate intended to come into surface abutment against the glenoid cavity of a patient's scapula and inside which is formed a central hole for guiding the bit. Thanks to this tool, the surgeon is able to hollow out an incipient canal. This document also describes, with reference to FIGS. 15 to 17 thereof, another tool comprising a plate for abutment on the scapula, inside which are formed three successive guide holes for a bit. The surface of the plate facing towards the scapula is provided with a projection adapted to be housed in the incipient canal previously hollowed out. By successive applications of the drill at the level of each of the three holes, the surgeon disengages a considerable volume of osseous matter and thus hollows out a sufficiently large canal for receiving the keel of the glenoid implant envisaged in this document.

Depending on the patient's morphology, the state of the scapula on which a glenoid implant is intended to be positioned, the operating conditions and/or the exact shape of the implant to be positioned, the longitudinal direction of the canal for receiving the keel of the implant is different. In general, the surgeon should hollow out a canal in the direction where the patient's scapula is the most resistant, particularly in a thick zone where the bone is abundant and healthy.

At the present time, the direction for hollowing out this canal is determined on the scapula either by rule of thumb by the surgeon or, when he is using a tool such as the one described in afore-mentioned document U.S. Pat. No. 6,379,386, is arbitrarily imposed by the plate of the tool used. If the surgeon attempts to apply the drilling member in a chosen direction without using a guiding tool, he runs the risk of the drilling member slipping and/or making a canal in a direction different from the one which he was intending, less favourable for the positioning and subsequent hold of the glenoid implant.

It is an object of the present invention to propose an ancillary tool of simple structure which makes it possible to impose on the drilling, fashioning or like member used during the positioning of a glenoid implant, for example on the bit of a surgical drill, a direction of application chosen by the surgeon, if necessary pre-operatively, over a whole range of possible directions, and even for any anatomically conceivable direction.

SUMMARY OF THE INVENTION

To that end, the invention relates to an ancillary tool for positioning a glenoid implant, of the type comprising a plate which defines a bearing surface intended to abut against the glenoid cavity of a patient's scapula and which forms a directional guide for a drilling, fashioning or like member, characterized in that it comprises means for adjusting the direction of the guide with respect to the plate.

By manipulating these adjusting means, the surgeon has available a guiding adjusted in the direction which he will have previously chosen, for example after analysis of scanner images of the scapula made before the surgical operation. When these adjusting means are adapted to be removably connected to the plate, the surgeon can adjust the direction of guiding imposed on the drilling member used, just before the operation or if necessary preoperatively.

In accordance with other characteristics of this ancillary tool, taken separately or in any technically possible combinations:

- the means for adjusting the direction of the guide are adapted to be received and immobilized in a through opening formed in the plate and opening out on the bearing surface of the plate.
- the adjusting means make it possible to adjust the direction of the guide with respect to the plate at least in two planes which are substantially perpendicular to each other.
- the means for adjusting the direction of the guide comprise a barrel provided with a plurality of rectilinear through holes, one of said holes forming the directional guide for the drilling, fashioning or like member.
- the barrel comprises a tubular body closed at one of its ends by a bottom, the through holes being formed in the bottom and opening out inside the tubular body, which tubular body presents in transverse section an outer profile adapted to cooperate with a through opening of the plate so as to immobilize the barrel in this opening.
- the axes of the holes are substantially concurrent at a point located substantially in the geometrical extension of the convex face of the plate.
- a first series of holes in the barrel is aligned along a first plane and a second series of other holes in the barrel is aligned along a second plane substantially at right angles to the first plane.
- in each of the first and second series of holes, the axes of the holes located on the same side of the central axis of the barrel are offset angularly with respect to one another by a substantially constant value.
- other series of holes are provided in the quadrants defined by the first and second series of holes.
- the means for adjusting the direction of the guide comprise, on the one hand, an element mobile with respect to the plate and, on the other hand, an element for immobilizing the element mobile with respect to the plate, the mobile element being provided with a rectilinear through bore adapted to form the directional guide for the drilling, fashioning or like member.

the direction of the bore of the mobile element is continuously adjustable.

the mobile element presents a surface adapted to cooperate with an associated surface of the plate.

the surface of the mobile element adapted to cooperate with the associated surface of the plate is substantially spherical.

it further comprises a tool for controlling the immobilizing element.

it further comprises means for displacing and positioning the mobile element with respect to the plate adapted to lead the bore of the mobile element substantially in a chosen direction.

the means for displacing and positioning the mobile element comprise a rigid retaining support for the plate and a rod for driving the mobile element, adapted to be displaced with respect to the rigid support, said support being provided with two protractors adapted to plot the angular position of the rod in two planes substantially perpendicular to each other.

The invention also relates to a method for positioniong a glenoid implant, in which:

at least one scanner image or the like of a patient's scapula is available, a preferential direction of application on the scapula of a drilling, fashioning or like member is determined, an ancillary guiding tool which comprises a plate forming a directional guide for said drilling member and means for adjusting the direction of the guide with respect to the plate, are used, a surface of the plate is applied on the glenoid cavity of the scapula, the drilling member is introduced in the guide of which the direction is adjusted to the preferential direction, and the drilling member is actuated so as to act on the scapula in the preferential direction.

In accordance with two variants of this method:

the adjusting means of the ancillary guiding tool comprise a barrel provided with a plurality of rectilinear through holes, and in which, after the plate has been applied on the glenoid cavity of the scapula, the drilling member is introduced in the hole which, among the through holes of the barrel, extends in a direction close to or the direction the closest to the preferential direction; or the adjusting means of the ancillary guiding tool comprise an element mobile with respect to the plate and an element for immobilizing the element mobile with respect to the plate, said mobile element being provided with a rectilinear through bore, and in which, before the plate has been applied on the glenoid cavity of the scapula, the mobile element is positioned with respect to the plate so as to lead the bore of the mobile element substantially in the preferential direction, then the element mobile with respect to the plate is immobilized via the immobilizing element.

BRIEF DESCRIPTION OF THE DRAWINGS

The invention will be more readily understood on reading the following description given solely by way of example and made with reference to the accompanying drawings, in which.

DESCRIPTION OF PREFERRED EMBODIMENTS

Figure 1:
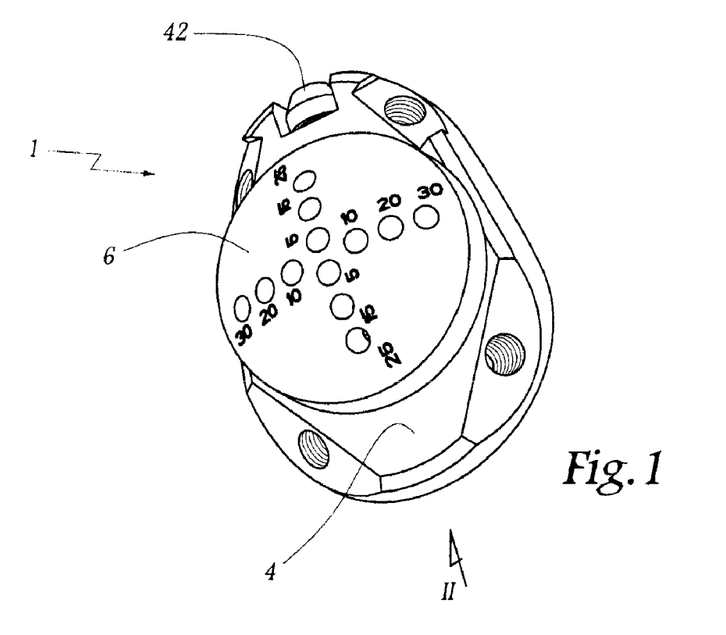
FIG. 1 is a view in perspective of a first form of embodiment of an ancillary tool according to the invention.
Figure 2:
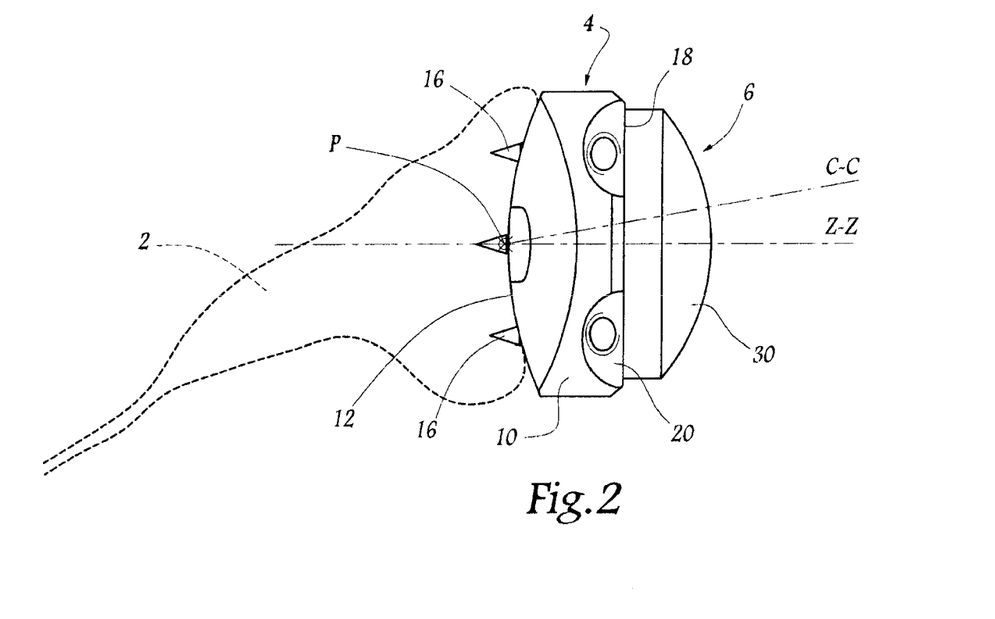
FIG. 2 is a view in elevation, taken in the direction of arrow II indicated in FIG. 1, of the ancillary tool applied on a scapula of a human being.

Referring now to the drawings, FIG. 1 firstly shows an ancillary tool 1 for positioning a glenoid implant, adapted to directionally guide the bit of a surgical drill (not shown). When positioning a glenoid implant on a patient's scapula, with a view to forming a shoulder prosthesis, the surgeon must hollow out in the glenoid cavity of the scapula a canal for receiving a keel of the glenoid implant. As a function of the patient's morphology, the geometry of this keel, the pathology having motivated the positioning of the implant, etc. . . . , the direction in which this canal is to be formed is different. In order to determine the optimal direction of this canal, the term "optimal" here meaning "preferential" considering all the medical parameters brought to his knowledge, the surgeon has available for example a series of scanner images of the scapula on which it is provided to position the implant and he determines this privileged direction. The exact localization of the point of application of the drilling member is secondary with respect to the privileged direction, it being understood that this point of application lies in a central zone of the glenoid cavity. FIG. 2 shows in dotted lines a patient's scapula 2 as it appears to the surgeon by a scanner image. Axis C-C indicates the privileged direction chosen by the surgeon as being the direction in which the drilling member should be applied.

To that end, the ancillary tool 1 essentially comprises a plate 4 on which are added means 6 for adjusting the direction of a drilling guide with respect to the plate.

More precisely, as shown in FIGS. 1 to 5, the plate 4 is formed by a metal body 10 presenting, in a direction noted Z-Z, a smaller dimension than in the two remaining orthogonal directions, indicated by axes X-X and Y-Y. In the following description, the terms lower and upper will be oriented with respect to axis X-X, with the result that, for example with reference to FIG. 3, the term upper corresponds to the top part of this Figure, while the term lower corresponds to the bottom part.

The body 10 of the plate 4 defines a convex surface 12 intended to come into surface abutment against the scapula 2, as shown in FIG. 2. The surface 12 is advantageously provided with projecting barbs 16 intended to facilitate retention of the plate with respect to the scapula as will be explained hereinafter.

Figure 3:
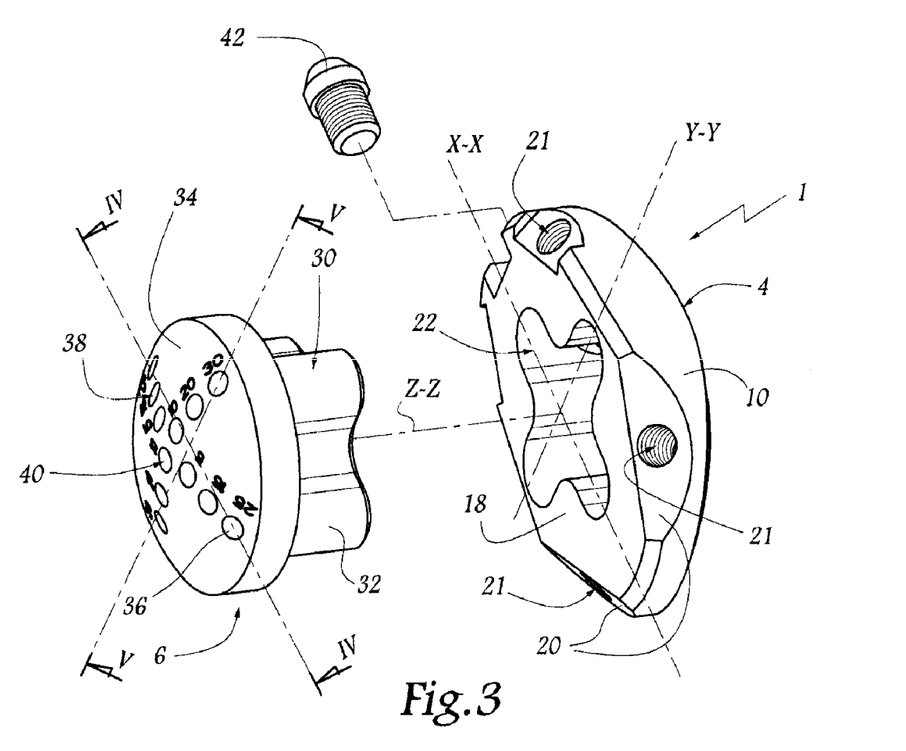
FIG. 3 is a exploded view in perspective of the ancillary tool of FIG. 1.

The body 10 defines a surface 18 opposite the surface 12, which is substantially planar and from which bevelled surface 20 are made at the four corners of the body 10. In these surfaces 20 there are formed tapped recesses 21 adapted to receive means (not shown) for removably fixing a handle for manipulating the plate, known per se.

The body 10 internally defines a through opening 22, of central axis Z-Z and of cruciform profile in cross-section. More precisely, the opening 22 comprises two pairs of diametrically opposite lobes, the lobes of the same pair being respectively aligned in directions X-X and Y-Y.

Figure 4:
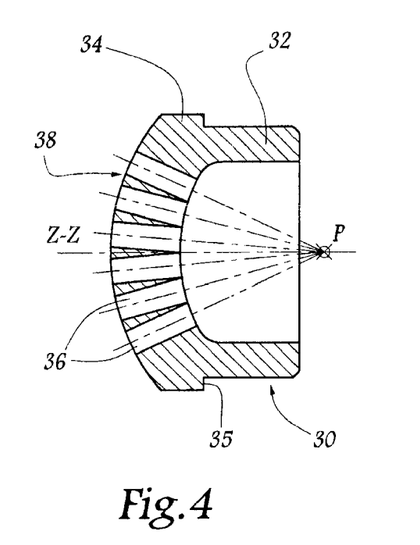
FIGS. 4 and 5 are sections along the planes indicated IV and V in FIG. 3.
Figure 5:
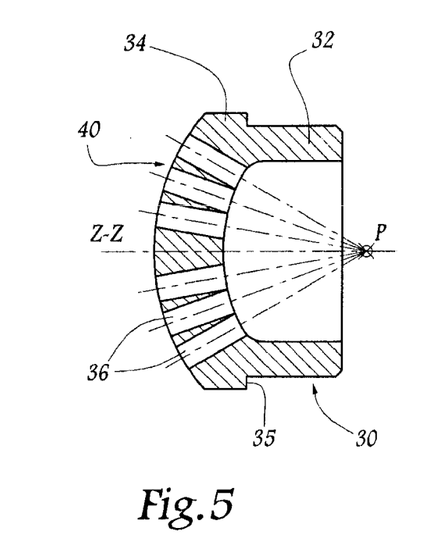

The adjusting means 6 are formed by a barrel 30 shown in greater detail in FIGS. 3 to 5. This barrel comprises a tubular body 32 of axis Z-Z and whose outer profile is substantially complementary of the profile of the through opening 22 of the body 10. The body 32 is closed at one of its ends by a substantially hemispherical bottom 34 which, with the outer surface of the body 32, forms a planar shoulder 35 radially projecting with respect to axis Z-Z.

Inside this bottom 34 are formed rectilinear through holes 36 of which the respective axes are substantially concurrent at a point P lying on axis Z-Z. These holes 36 are distributed in a first series 38 of holes which extend in a first plane containing the axes X-X and Z-Z and corresponding substantially to the plane of section of FIG. 4, and a second series 40 of holes which extend in a second plane containing axes Y-Y and Z-Z and corresponding to the plane of section of FIG. 5.

In each series 38, 40 of holes 36, the value of the angular deviation between two adjacent holes located on the same side of axis Z-Z is substantially 10°. The value of the angular deviation between axis Z-Z and one of the two holes 36 of the series 38 located nearest the centre of the bottom 34 is about 5°, while the value of the same angular deviation for the two holes nearest the centre of series 40 is about 10°.

By cooperation of the tubular body 32 with the through opening 22 of the plate 10, the barrel 30 is able to be received and immobilized with respect to the plate 4, the shoulder 35 in that case being positioned in abutment against the substantially planar surface 18 of the plate, as shown in FIG. 2. Point P is then inscribed substantially in the geometric extension of the face 12 intended to come into abutment against the scapula 2.

In the upper part of the plate 4, a screw 42 is housed in a complementary bore extending in direction X-X and opening out, on one side, on the edge of the body 10 and, on the other side, in the opening 22.

This screw makes it possible to retain the barrel 30 in the opening 22 along axis Z-Z.

The use of the ancillary tool 1 when positioning a glenoid implant for shoulder prosthesis is as follows:

When the surgeon has determined, for example by means of scanner images of a patient's shoulder, the privileged direction C-C in which he desires to anchor the glenoid implant in the scapula and therefore to apply a drill bit, he applies the ancillary tool 1 against the scapula. More precisely, the surface 12 of the plate 4 is applied against the osseous glenoid cavity of the scapula 2, as shown in FIG. 2. To that end, the ancillary tool 1 is advantageously manipulated by a handle connected to the plate 10 at the level of the bevelled surfaces 20. The barbs 16 facilitate attachment of the plate with respect to the scapula.

While the barrel 30 is being received and immobilized in the opening 22 of the plate, the surgeon selects, from all the holes 36 of the barrel, the single hole whose longitudinal axis is the closest to the preferential direction C-C which he has chosen. If necessary, the surgeon disengages the barrel 30 from the plate, pivots it through a quarter turn then replaces it in the cruciform opening 22, which makes it possible to have available drilling directions adjustable with a pitch of 5° in the two planes containing axes X-X and Z-Z and axes Y-Y and Z-Z, respectively.

In FIG. 2, the chosen direction C-C forms, in a plane containing axes Y-Y and Z-Z, an angular deviation of about 15° with respect to the central axis of the glenoid cavity, with the result that the surgeon will use one of the holes of the series 38 of the barrel only.

He then introduces the bit of a drill into this hole in order to make a bore or at least an incipient bore in the direction imposed by the hole. If necessary, after having disengaged the ancillary tool 1, the surgeon may widen the orifice bored in the scapula by a bit of larger diameter or another fashioning member. He may also use a milling tool which, wedged in the bored orifice, enables a glenoid resection plane orthogonal to direction C-C to be made.

The ancillary tool 1 is thus easy to use and rapidly provides the surgeon with a guide for application of a member, particularly a drill, whose direction is adjusted in the preferential direction that the surgeon has chosen.

Figure 6:
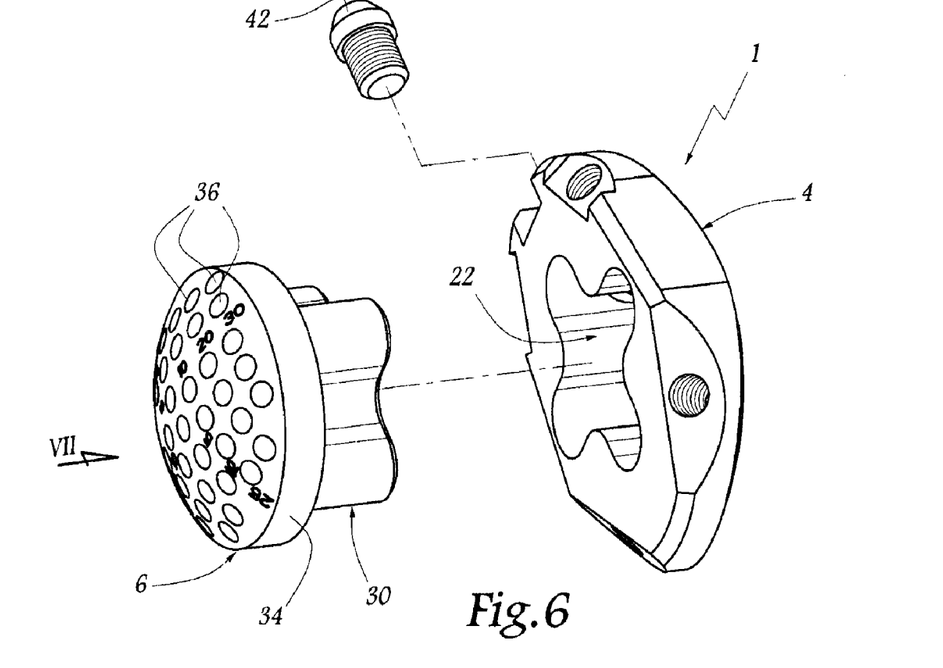
FIG. 6 is a view similar to FIG. 3 of a variant embodiment of the ancillary tool of FIG. 1.
Figure 7:
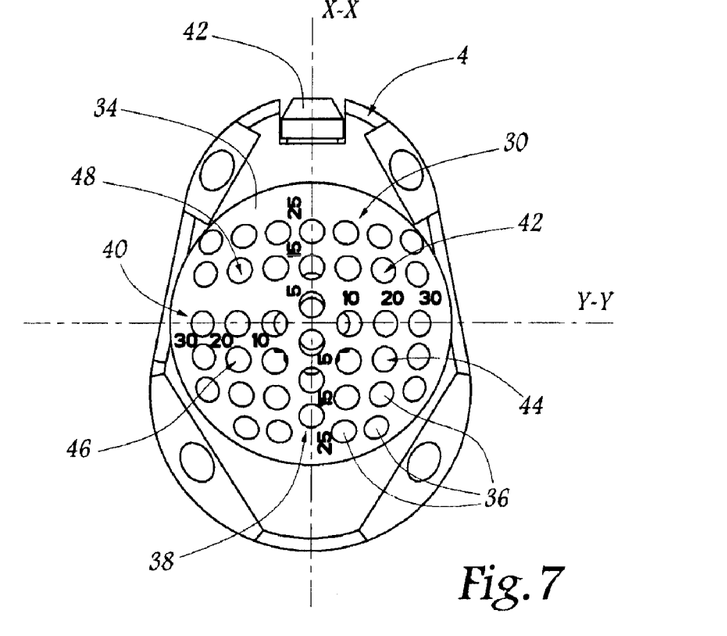
FIG. 7 is a view in elevation taken in the direction of arrow VII indicated in FIG. 6.

FIGS. 6 and 7 show a variant embodiment of the ancillary tool 1 which differs from the tool of the preceding Figures by the number and arrangement of the guiding holes 36 made in the barrel 30. In addition to the series of holes 38 and 40, series of holes 42, 44, 46 and 48 are respectively located in the four quadrants defined by the series of holes 38 and 40, forming a grid layout of the bottom 34 of the barrel. This variant offers the surgeon more guiding directions than the tool of FIGS. 1 to 5.

FIGS. 8 to 14 show a second ancillary tool 50 according to the invention. This tool is intended to be used within the same framework as the tool 1 of the preceding Figures, i.e. to guide the rod of a member, particularly the bit of a surgical drill, when positioning a glenoid implant of a shoulder prosthesis.

As shown in detail in FIGS. 8 to 11, this tool 50 comprises a plate 52 formed by a metal body 54 having substantially the same shape as the body 10 of the plate 4 and oriented with respect to axes X-X, Y-Y and Z-Z defined in the same way as in FIG. 3.

The body 54 defines a convex surface 56 intended to abut against a patient's osseous glenoid cavity, advantageously provided with catching barbs 58 substantially similar to barbs 16 of the plate 10, as well as an opposite planar surface 59. The body 54 is also adapted to be removably fixed to a handle for manipulation (not shown).

Figure 9:
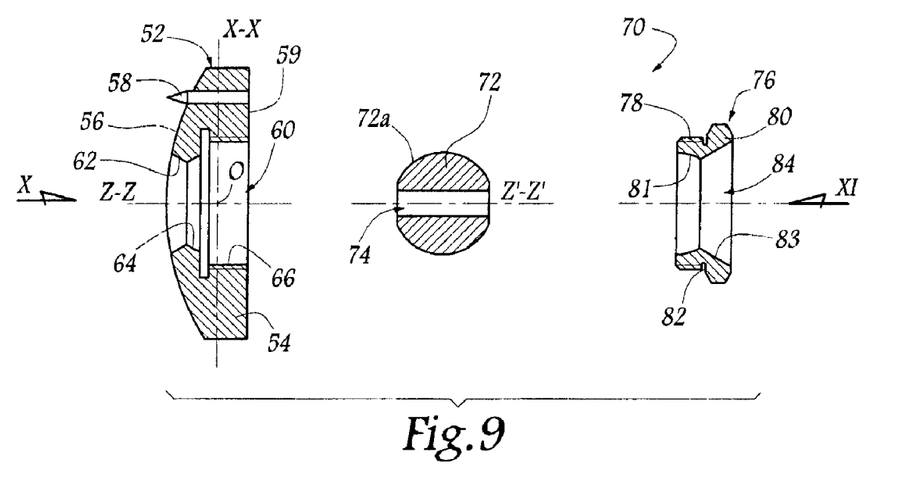
FIG. 9 is a view in longitudinal section of certain elements of the ancillary tool of FIG. 8, shown on a larger scale.
Figure 10:
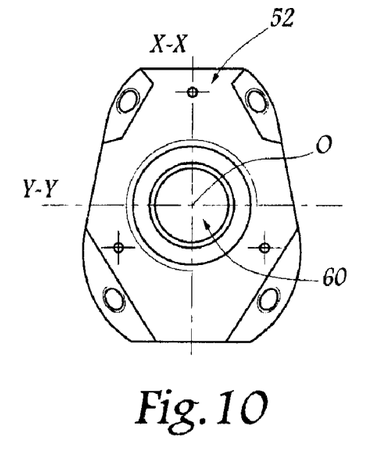
FIG. 10 is a view in elevation, taken in the direction of arrow X indicated in FIG. 9, of the element to which this arrow X is pointing.
Figure 11:
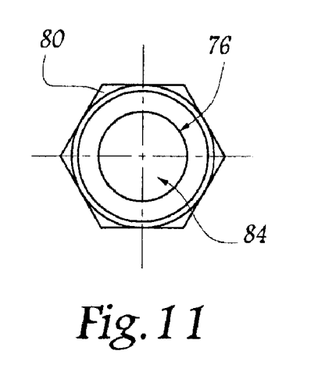
FIG. 11 is a view in elevation, taken in the direction of arrow XI indicated in FIG. 9, of the element to which this arrow XI is pointing.

In the body 54 of the plate 52 there is formed a through opening 60 of axis of revolution Z-Z. As shown in FIG. 9, this opening comprises, successively from the face 56 of the body 54, a truncated part 62 which diverges towards the face 56, a part 64 in the form of a frustum of sphere with centre O, and a tapped cylindrical part 66.

The tool 50 also comprises means 70 for adjusting the direction of a bore guide with respect to the plate 52, comprising, on the one hand, a sphere 72 pierced right through along one of its diameters, forming a single cylindrical bore 74 of axis Z'-Z', and, on the other hand, a nut 76.

More precisely, the sphere 72 presents an outer surface 72*a* substantially complementary of the hemispherical part 64 of the opening 60. The nut 76 is formed by a tubular body 78, of axis Z-Z and threaded in manner substantially complementary of the tapped cylindrical part 66 of the opening 60, and by a hexagonal head 80 which forms with the tubular body 78 a shoulder 82 radially projecting with respect to the axis of the body 78. The nut 76 internally forms a bore 84 formed, on the tubular body 78 side, by a part 81 substantially in the form of a frustum of sphere complementary of the outer surface of the sphere 72, and, on the head 80 side, by a flared part 83.

By cooperation of the outer surface 72*a* of the sphere 72 with the surface 64 of the opening 60, the sphere 72 is mobile with respect to the plate 52 in the manner of a ball-joint of centre O. Moreover, by engagement and cooperation of the threads of the body 78 of the nut 76 and of the tapped part 66 of the opening 60, the nut is able to immobilize the sphere 72 with respect to the plate. The planar face 59 of the plate forms a stop surface for the shoulder 82, thus avoiding excessive tightening, and even the deterioration of the sphere by the tightened nut.

Figure 12:
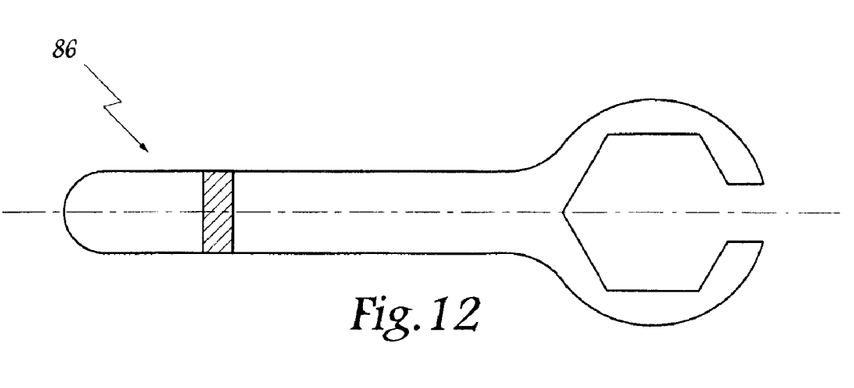
FIG. 12 is a view in elevation of a tool used during the manipulation of the ancillary tool of FIG. 8.

In order to make it possible to apply a considerable tightening torque on the nut 76, the ancillary tool 50 advantageously comprises a spanner 86, shown in FIG. 12, provided with a hollowed head for driving the hexagonal head of the nut.

The sphere 72 being mobile with respect to the plate 52 when the nut 76 is not tightened, this sphere is adapted to be displaced so that the axis Z'-Z' of its bore 74 is adjusted in the privileged direction C-C previously chosen by the surgeon.

Figure 8:
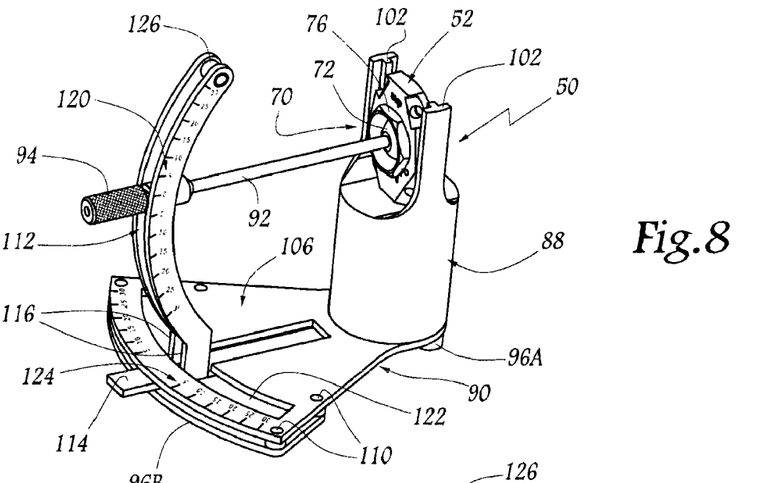
FIG. 8 is a view in perspective of a second form of embodiment of an ancillary tool according to the invention.
Figures 13, 14:
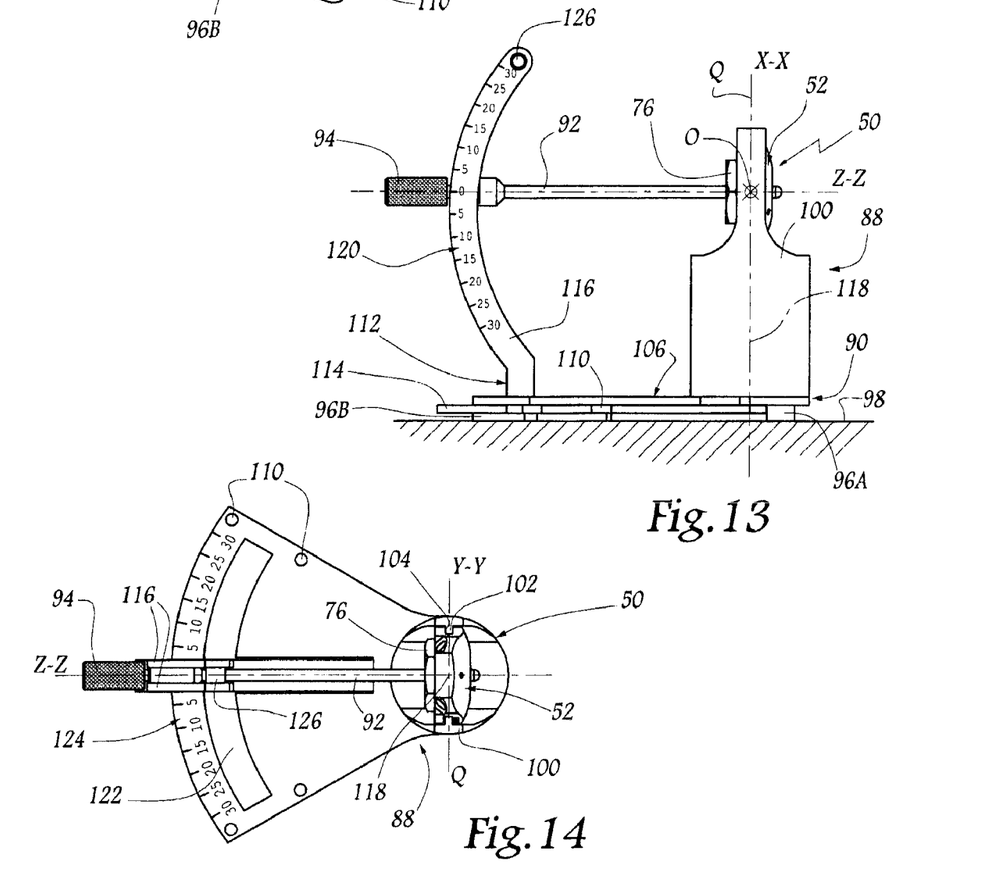
FIG. 13 is a view in side elevation of the ancillary tool of FIG. 8.
FIG. 14 is a plan view of the ancillary tool of FIG. 8.

The ancillary tool 50 further comprises means 88 for displacing and positioning the sphere 72 with respect to the plate 52, shown in FIGS. 8, 13 and 14. These means comprise a rigid support 90, on the one hand, and a rod 92 for driving the sphere 72, on the other hand, connected to the support 88.

More precisely, the rod 92 is adapted, at one of its ends, to be fitted inside the bore 74 of the sphere 72, and comprises at its other end a knurled knob 94 for manipulating the rod, removably connected on this rod in the manner of a nut.

As for the rigid support 90, it comprises:
- a lower support for bearing on a substantially planar surface, only shown in FIG. 13 under reference 98, formed for example by a table or other like work surface; this lower support is constituted for example by a foot 96A and a heel 96B;
- a base 100 for receiving and immobilizing the plate 52, provided with a U of which the parallel arms each bear a longitudinal rib 102 adapted to be received in a corresponding groove 104 formed in the lateral edges of the body 54 of the plate, as shown in FIG. 14, so as to position the plane Q of the plate, containing point 0 and the axes X-X and Y-Y, substantially perpendicularly to the planar surface 98;
- a so-called horizontal protractor 106 in the form of a plate substantially parallel to the planar surface 98; this horizontal protractor 106 is, on the one hand, joined to the base 100 and, on the other hand, fixedly connected to the heel 96B of the lower bearing support by fastening studs 110;
- a so-called vertical protractor 112 constituted by a flat bar 114 interposed between the heel 96B and the plate of the horizontal protractor 106, and by a pair of arms 116 parallel to each other, which extend transversely from the bar 114 and between which the rod 92 is retained.

The bar 114 is mounted to pivot with respect to the rest of the support 90, about a pivot axis 118 perpendicular to the surface 98 and formed for example by a cylindrical stud guided in rotation in a corresponding recess formed in the plate of the horizontal protractor 106 and the base 100.

Depending on its length, each arm 116 presents an essentially semi-circular profile of centre O and bears corresponding angle graduations, referenced 120 in FIGS. 8 and 13. The graduation zero corresponds to the position of the rod 92 perpendicular to the plane Q. At the level of their ends connected to the pivoting plate 114, the arms 116 are received in a groove 122 of the horizontal protractor 106, which is semi-circular and centred on the pivot axis 118. The periphery of the groove 122 bears angular graduations referenced 124. The graduation zero corresponds to the position of the rod 92 perpendicular to the plane Q. At their opposite ends, the arms 116 are connected by a joining bridge 126.

Use of the ancillary tool 50 when positioning a glenoid implant for a shoulder prosthesis is as follows:

In the same way as for the ancillary tool 1 of FIGS. 1 to 5, the surgeon determines the privileged direction C-C in which he wishes to proceed with hollowing out the canal for receiving a keel of the glenoid implant.

Starting from the configuration of the tool 50 shown in FIGS. 8, 13 and 14, in which the plate 52 is immobilized in the base 100 of the support 90, the surgeon, after having, if necessary, slightly loosened the nut 76, drives the sphere 72 by means of the rod 92. By displacing the knurled knob 94 upwardly or downwardly with respect to the planar surface 98, the inclination of the rod in a plane perpendicular to axis Y-Y is adjusted. By displacing the knob 94 to the left or to the right in a plane parallel to the planar surface 98, the whole of the vertical protractor 112 pivots about the axis 118 and the angular orientation of the rod in a plane perpendicular to axis X-X of the plate is adjusted. The surgeon verifies that the rod is correctly positioned angularly by directly reading on the corresponding angular references 120 and 124.

Once the rod 92 is directed in the chosen direction, the surgeon uses the spanner 86 to tighten the nut 76 firmly and thus immobilize the sphere 72 with respect to the plate 52. To that end, the head of the spanner 86 is provided with a sufficiently wide slot to enable the spanner to engage on the head 80 of the nut without being hindered by the rod 92.

The surgeon then disengages the plate 52 from the base 100, by removing for example the plate, the sphere 72, the tightened nut 76 and the rod 92, by previously unscrewing the knob 94. The rod 92 is then withdrawn from the hole 74 without difficulty.

In the same way as for the ancillary tool 1 of FIGS. 1 to 5, the surgeon then places the plate 52 in surface abutment against the patient's osseous glenoid cavity and introduces a drill bit inside the hole 74.

The second form of embodiment of the ancillary tool 50 presents the advantage over the tool 1 of FIGS. 1 to 5, of allowing the surgeon to continuously adjust the direction of the drill guide in all anatomically conceivable directions, and not only in a discrete series of these directions.

Various arrangements and variants of the two forms of embodiment of the ancillary tool described hereinabove may, furthermore, be envisaged. By way of example, the bearing face 12 or 56 is planar. Moreover, the positions of points P and O mentioned above may diverge somewhat from those described hereinabove. By way of variant, the adjusting means 70 employing a sphere are replaced by a system employing a slideway allowing directional adjustment in a single plane.

Similarly, the ancillary tool according to the invention is able to directionally guide any drilling, fashioning or like member other than a drill bit, for example an impact pin or a marking pin.

What is claimed is:

1. An ancillary tool for positioning a glenoid implant on a prepared surface of a glenoid cavity, the ancillary tool comprising:
- a base plate comprising a primary opening and a bearing surface adapted to engage with the prepared surface of the glenoid cavity;
- a drilling guide engaged with the primary opening and movable through at least two degrees of freedom relative to the base plate, such that at least a portion of the prepared surface is accessible through the primary opening and a guide hole in the drilling guide when the base plate is engaged with the glenoid cavity; and
- a securing mechanism adapted to releasable secure the drilling guide relative to the base plate.

2. The ancillary tool of claim 1 wherein the guide is moveable through at least two degrees of freedom comprise rotation around an X-axis and an Y-axis.

3. The ancillary tool of claim 1 wherein the guide pivotally engages with the base plate.

4. The ancillary tool of claim 1 comprising angular references indicating a position of the guide relative to the base plate.

5. The ancillary tool of claim 1 comprising angular references wherein graduation zero corresponds to the guide hole substantially perpendicular to the bearing surface.

6. The ancillary tool of claim 1 comprising an angular positioning device operably coupled to the guide.

7. The ancillary tool of claim 1 comprising a horizontal guide component and a vertical guide component operably coupled to the guide.

8. The ancillary tool of claim 1 comprising: an angular positioning device operably coupled to the base plate; and
- a rod operatively coupling the angular positioning device to the guide.

9. The ancillary tool of claim 1 comprising a rod operatively coupled to the guide hole.

10. The ancillary tool of claim 1 wherein the bearing surface on the base plate is convex.

11. The ancillary tool of claim 1 wherein the bearing surface comprises at least one feature that releasably secures the base plate to the prepared surface of the glenoid cavity.

12. The ancillary tool of claim 1 wherein the bearing surface comprises a plurality of barbs that releasably secure the base plate to the prepared surface of the glenoid cavity.

13. The ancillary tool of claim 1 comprising a fastener adapted to retain the guide in the primary opening.

14. The ancillary tool of claim 1 wherein at least a portion of the guide and at least a portion of the primary opening comprise complementary cross-sections.

15. The ancillary tool of claim 1 wherein the guide comprises a sphere.

16. The ancillary tool of claim 1 wherein the guide hole comprise one of a drilling guide or a marking guide.

17. The ancillary tool of claim 1 comprising one or more of a drill bit, an impact pin, or a marking pin located in the guide hole.

18. The ancillary tool of claim 1 comprising a base adapted to receive and secure the base plate.

19. The ancillary tool of claim 18 comprising a horizontal guide component and a vertical guide component operably coupled to the base.

20. An ancillary tool for positioning a glenoid implant on a prepared surface of a glenoid cavity, the ancillary tool comprising:
- a positioning rod slidably engaged with a horizontal guide component and a vertical guide component;
- a joint component coupleable with the positioning rod; and
- a base plate comprising a bearing surface adapted to be releasably secured to the prepared surface of the glenoid cavity, wherein the base plate defines an opening configured to receive at least a portion of the joint component such that the joint component is able to articulate in the opening of the base plate in at least two degrees of freedom.

* * * * *